(12) United States Patent
Bond et al.

(10) Patent No.: US 7,576,019 B2
(45) Date of Patent: *Aug. 18, 2009

(54) FIBERS, NONWOVENS AND ARTICLES CONTAINING NANOFIBERS PRODUCED FROM HIGH GLASS TRANSITION TEMPERATURE POLYMERS

(75) Inventors: Eric Bryan Bond, Maineville, OH (US); Rajeev Chhabra, Mason, OH (US); Olaf Erik Alexander Isele, West Chester, OH (US); Han Xu, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 251 days.

This patent is subject to a terminal disclaimer.

(21) Appl. No.: 11/109,393

(22) Filed: Apr. 19, 2005

(65) Prior Publication Data

US 2006/0084340 A1    Apr. 20, 2006

Related U.S. Application Data

(60) Provisional application No. 60/563,355, filed on Apr. 19, 2004.

(51) Int. Cl.
    *D04H 1/00* (2006.01)
(52) U.S. Cl. ................................ 442/341
(58) Field of Classification Search ......... 442/340, 442/351, 327, 331, 332, 333, 334, 341; 428/365, 428/401
    See application file for complete search history.

(56) References Cited

U.S. PATENT DOCUMENTS

| | | | |
|---|---|---|---|
| 4,818,464 A | 4/1989 | Lau | |
| 4,923,454 A | 5/1990 | Seymour et al. | |
| 4,937,020 A | 6/1990 | Wagner et al. | |
| 5,935,883 A | 8/1999 | Pike | |
| 6,183,670 B1 | 2/2001 | Torobin et al. | |
| 6,269,513 B1 | 8/2001 | Torobin | |
| 6,395,046 B1 | 5/2002 | Emig et al. | |
| 6,695,992 B2 | 2/2004 | Reneker | |
| 2002/0035354 A1* | 3/2002 | Mirle et al. | 604/385.01 |
| 2003/0168401 A1 | 9/2003 | Koslow | |
| 2003/0177909 A1 | 9/2003 | Koslow | |
| 2004/0092185 A1* | 5/2004 | Grafe et al. | 442/153 |
| 2005/0053782 A1 | 3/2005 | Sen et al. | |
| 2007/0021021 A1* | 1/2007 | Verdegan et al. | 442/334 |

FOREIGN PATENT DOCUMENTS

| | | |
|---|---|---|
| JP | 3249207 A2 | 11/1991 |
| JP | 08-144166 A | 6/1996 |
| JP | 2668963 B2 | 10/1997 |
| JP | 2001-104372 A | 4/2001 |
| WO | WO 00/22207 | 4/2000 |
| WO | WO 03/043809 A1 | 5/2003 |
| WO | WO 2004/020722 A2 | 3/2004 |

OTHER PUBLICATIONS

U.S. Appl. No. 10/877,538, filed Jun. 25, 2004, Isele et al.
U.S. Appl. No. 10/877,540, filed Jun. 25, 2004, Isele et al.
U.S. Appl. No. 10/877,458, filed Jun. 25, 2004, Isele et al.
U.S. Appl. No. 10/877,462, filed Jun. 25, 2004, Chhabra et al.
U.S. Appl. No. 10/877,463, filed Sep. 10, 2004, Chhabra et al.
U.S. Appl. No. 11/109,557, filed Apr. 19, 2005, Isele et al.
U.S. Appl. No. 11/109,554, filed Apr. 19, 2005, Bond et al.
Fiber Handbook, Raw Materials, III. Production section (II), Edited by the Fiber Society, Maruzen Co., Ltd.

\* cited by examiner

*Primary Examiner*—Arti Singh-Pandey
(74) *Attorney, Agent, or Firm*—Jay A. Krebs; Angela Marie Stone

(57) ABSTRACT

The present invention is directed to nonwoven webs and articles comprising nanofibers. The nanofibers are made from a polymer having a glass transition temperature about 25 C. The nanofibers, having a diameter of less than 1 micron, may comprise a significant number of the fibers in one layer of the web contained by the article. Preferably, the nanofibers are produced in a melt film fibrillation process. Articles include diapers, training pants, adult incontinence pads, catamenials products such as feminine care pads and pantiliners, tampons, personal cleansing articles, personal care articles, and personal care wipes including baby wipes, facial wipes, and feminine wipes.

10 Claims, No Drawings

FIBERS, NONWOVENS AND ARTICLES CONTAINING NANOFIBERS PRODUCED FROM HIGH GLASS TRANSITION TEMPERATURE POLYMERS

CROSS-REFERENCE TO RELATED APPLICATIONS

This application claims the benefit of U.S. Provisional Application No. 60/563,355, filed Apr. 19, 2004.

FIELD OF THE INVENTION

The present invention relates to fibers, nonwovens and articles made from nanofibers and method of producing the nanofibers. The nanofibers can be made from high glass transition temperature polymers.

BACKGROUND OF THE INVENTION

The need for articles produced from nonwoven containing nanofibers has continued to increase. The diameters of nanofibers are generally understood to be less than about 1000 nanometer or one micron. The nanofibers webs are desired due to their high surface area, low pore size, and other characteristics. The nanofibers, also commonly called microfibers or very fine fibers, can be produced by a variety of methods and from a variety of materials. Although several methods have been used, there are drawbacks to each of the methods and producing cost effective nanofibers has been difficult.

Methods of producing nanofibers include a class of methods described by melt fibrillation. Non limiting examples of melt fibrillation methods include melt blowing, melt fiber bursting, and melt film fibrillation. Methods of producing nanofibers, not from melts, are film fibrillation, electro-spinning, and solution spinning. Other methods of producing nanofibers include spinning a larger diameter bi-component fiber in an islands-in-the-sea, segmented pie, or other configuration where the fiber is then further processed so that nanofibers result.

Melt fibrillation is a general class of making fibers defined in that one or more polymers are molten and extruded into many possible configurations (e.g. co-extrusion, homogeneous or bicomponent films or filaments) and then fibrillated or fiberized into filaments.

Melt blowing is a commonly used method of producing fibers. Typical fiber diameters range from 2 to 8 micron. Melt blowing can be used to make fibers with smaller diameters but with considerable changes needed to the process. Commonly, redesigned nozzles and dies are needed. Examples of these include U.S. Pat. Nos. 5,679,379 and 6,114,017 by Fabbricante et al. and U.S. Pat. Nos. 5,260,003 and 5,114,631 by Nyssen et al. These methods utilize relatively high pressures, temperatures, and velocities to achieve the small fiber diameter.

Melt fiber bursting is a derivative of mineral fiber making process that has been applied to polymer fiber making. Examples of mineral melt fiber bursting process include U.S. Pat. No. 4,001,357 by Walz et al. and U.S. Pat. Nos. 4,337,074 and 4,533,376 by Muschelknautz et al. The key to this process is the use of sonic and supersonic air (gas) velocities to burst the melt filament into a multiplicity of fine fibers. Typical fiber diameters range from less than 1 micron to about 6 micron. Examples of processes with bursting polymer melt into fine fibers include U.S. Pat. No. 5,075,161 by Nyssen et al.; European Patent Nos. 1 192 301 B1 and 0 724 029 B1 and European Patent Application 1 358 369 A2 by Gerking; and WO 04/020722 by Sodemann et al. These methods utilize Laval nozzles to speed up the gas velocities to sonic and/or supersonic range. When polymer melt is exposed to such high gas velocities, it bursts into multiplicity of fine fibers. The processes are configured by use of desired process conditions and die and nozzle geometries to produce desired fiber sizes.

Melt film fibrillation is another method to produce fibers. A melt film is produced from the melt and then a fluid is used to form nanofibers from the melt film. Two examples of this method include Torobin's U.S. Pat. Nos. 6,315,806; 5,183,670; and 4,536,361; and Reneker's U.S. Pat. Nos. 6,382,526, 6,520,425 and 6,695,992, assigned to the University of Akron.

Film fibrillation is another method of producing nanofibers although not designed for the production of polymeric nanofibers to be used in nonwoven webs. U.S. Pat. No. 6,110,588 by Perez et al., assigned to 3M, describes of method of imparting fluid energy to a surface of a highly oriented, highly crystalline, melt-processed, solidified polymer film to form nanofibers. The films and fibers are useful for high strength applications such as reinforcement fibers for polymers or cast building materials such as concrete.

Electrospinning is a commonly used method of producing nanofibers. In this method, a polymer is dissolved in a solvent and placed in a chamber sealed at one end with a small opening in a necked down portion at the other end. A high voltage potential is then applied between the polymer solution and a collector near the open end of the chamber. The production rates of this process are very slow and fibers are typically produced in small quantities. Another spinning technique for producing nanofibers is solution or flash spinning which utilizes a solvent.

Two-step methods of producing nanofibers are also known. The first step is to spin a larger diameter multicomponent fiber in an islands-in-the-sea, segmented pie, or other configuration. The larger diameter multicomponent fiber is then split or the sea is dissolved so that nanofibers result in the second step. For example, U.S. Pat. No. 5,290,626 by Nishio et al., assigned to Chisso, and U.S. Pat. No. 5,935,883, by Pike et al., assigned to Kimberly-Clark, describe the islands-in-the-sea and segmented pie methods respectively. These processes involve two sequential steps, making the fibers and dividing the fibers.

To produce disposable articles containing nanofibers that are commercially advantageous, the cost of the nanofibers must be controlled. Equipment, process, process aids, and polymer costs can all be controlled. Therefore, it is an object of the invention to produce nanofibers which are low in cost. It is also desired to form products containing nanofibers for a variety of uses and benefits. The uses include executions such as a diaper, wipe, and absorbent material, among other uses.

SUMMARY OF THE INVENTION

One way of reducing the cost of the nanofiber is by leveraging the large-scale production of high glass transition polymers. High glass transition polymers have a broad range of molecular weights and are more easily produced and therefore, more widely available. Typically, high glass transition polymers are stronger, less abrasive or linting, and more stable. Therefore, an object of the present invention is to produce articles containing nanofibers produced from high glass transition temperature polymers.

It has been found that it is beneficial to achieve lower fiber diameters with high glass transition temperature polymers. This is because high glass transition polymers freeze in the final form at high temperatures which are above ambient conditions. This allows for smaller diameter fibers. High glass transition temperature polymers and high attenuation energies, such as high gas velocities, flow rates, and take up speeds, are used to create the nanofibers. Generally, all of these parameters must optimized to form the nanofibers.

The present invention is directed to fibers, nonwovens and articles comprising nanofibers. The nanofibers can be made from a single step melt fibrillation process with a polymer having a glass transition temperature above 25° C. The nanofibers, having a diameter of less than 1 micron, may comprise a significant number of the fibers in one layer of the web contained by the article. Preferably, the nanofibers are produced in a melt film fibrillation process. Suitable articles include diapers, training pants, adult incontinence pads, catamenials products such as feminine care pads and pantiliners, tampons, personal cleansing articles, personal care articles, and personal care wipes including baby wipes, facial wipes, and feminine wipes.

DETAILED DESCRIPTION OF THE INVENTION

The present invention relates to articles made from nanofibers. The nanofibers are produced from one or more thermoplastic polymers. The polymers of the present invention will have a glass transition temperature above 25° C., which is defined as room temperature. The glass transition temperature is defined as the temperature in which a polymeric material goes from glass like behavior to rubber like behavior. The method for measuring the glass transition temperature of a polymer or elastomeric compound is ASTM WK6737 DSC. The glass transition temperature is best realized when the sample undergoes mechanical deformation. Below the glass transition temperature the material is brittle with low strains before failure and a high overall bulk modulus. Above the glass transition temperature (hereafter referred to as Tg), the material is rubbery with increased elongation and lower overall bulk modulus.

Typically, it has been found that high Tg polymers freeze in shape better than low Tg polymers, such as polypropylene or polyethylene. The freezing of shape or solidification can be desired as it is a second thermodynamic mechanism for maintaining shape for crystallizable polymers. For crystallizable polymers, the polymer melt must be cooled for crystallization to occur, which has kinetic constraints on its rate due to thermodynamic and mobility constraints of polymer chains. Often these materials can be cooled fast enough that crystallization does not occur so that the material does not fibrillate or stick together once fibrillated. For high Tg polymers, it is not necessary for the material to crystallize. Once the material passes through its Tg, large scale molecular motions stops and the material is essentially in a solid glassy state below its Tg. A material may undergo both crystallization and passing through its Tg during processing.

In the present invention, high Tg polymers are preferred due to their increased ability to fibrillate at higher temperatures. The additional thermodynamic transition for solidification of these high Tg polymers is desirable. Alternatively, one application may desire the use of high Tg and low Tg polymers. This may enable some fibers to fibrillate easily (i.e. the high Tg polymers) and other fibers not to easily fibrillate (i.e. the low Tg polymers). A potential use of high Tg and low Tg polymers could be for using a web as an adhesive. The low Tg polymers may remain sticky creating a self sticking web or can be used as a coating. Alternative, all low Tg polymer fibers could be utilized for a self sticking web or coating. Other uses of high and low Tg polymers is for bonding, particularly for thermal bonding. Distinct areas of a web having low Tg and high Tg polymers will have different thermal bonding properties and therefore different performance. This may enable the different areas to be suitable for barrier, air permeability, absorbency, controlled delivery, opacity, mechanical properties, post-processing, thermal properties, and other characteristics.

Preferably, the Tg is greater than about 30° C., more preferably greater than 40° C. and most preferably greater than about 50° C. A most preferred range for melt flow rates is from about 1 decigram per minute to about 1000 decigram per minute. The melt flow rate is measured using ASTM method D-1238. Generally, the lower the melt flow rate the more preferred. Therefore, polymers with melt flow rates less than about 500 decigram per minute and 100 decigrams per minute are even more preferred.

Suitable thermoplastic polymers include any polymer suitable for melt spinning and having a high Tg. Nonlimiting examples of thermoplastic polymers include polystyrene and copolymers, polyester and copolymers (PET, PBT, PCT, PTT and copolymers), polyamides, polymethylmethacrylate and copolymers, polycarbonate and copolymers, polyimides and copolymers, polyphenyleneoxide and copolymers, polysulfones and copolymers, polyvinylchloride and copolymers, poly(ether ester ketones) and copolymers, poly(m-phenylene isophthalamide, poly(p-phenylene terephthalamide) biodegradable polymers including thermoplastic starch, polylactic acid, and combinations thereof. The homopolymer, copolymers, and blends thereof are included within this description. The most preferred polymers are polyesters, polystyrene and polyamides. These polymers may contain plasticizers so long as their Tg is above 25° C.

Optionally, the polymer may contain additional materials to provide other properties for the fiber. These may modify the physical properties of the resulting fiber such as elasticity, strength, thermal or chemical stability, appearance, absorbency, odor absorbency, surface properties, and printability, among others. A suitable hydrophilic melt additive may be added. Optional materials may be present up to 50% of the total polymer composition as long as the Tg of the polymer composition is still within the identified range.

The fibers of the present invention may be single- or multi-component fibers such as bicomponent fibers. The fibers may have a sheath-core or side-by-side or other suitable geometric configuration. After the fibers are made, the fibers may be treated or coated before formed into a web. Additionally, after a web is made, the web may be treated. Optionally, additives may be compounded into the polymer resin and these additives migrate out to the surface after the fibers are formed. The additives that move to the surface may need to be cured utilizing external energy, such as heat, or additives on surface may need to be chemically reacted with another component or curing may need to be catalyzed in the presence of another component, such that additional components may be added to the process while the fibers are being made or after the fibers are made using the resin with additives. Suitable treatments include hydrophilic or hydrophobic treatments. An example of hydrophobic treatment is poly-di-methyl-siloxanes. The specific treatment depends on the use of the web, type of polymer, and other factors. Desirable treatments are familiar to those skilled in the art.

The average fiber diameter of a significant number of fibers in the nanofiber layer of the web can be less than one micron and preferably from about 0.1 microns to 1 micron, more preferably from about 0.3 microns to about 0.9 microns. The basis weight of the nanofiber layer can be less than about 25 gsm, commonly from about 0.1 to about 15 gsm, preferably less than 10 gsm or 5 gsm. The nanofiber layer may have a basis weight in the range of from about 0.5 to about 3 gsm or from about 0.5 to about 1.5 gsm, depending upon use of the nonwoven web. It may be desired to form a web of several layers. The nanofiber layer may be combined with one, two, or more layers. A spunbond-nanofiber-spunbond web is one example. Basis weights for the total composite webs range from about 5 gsm to about 100 and are commonly from about 10 to about 50 gsm.

A uniform nanofiber web is typically desired and can be challenging to produce, particularly at low basis weights. Web uniformity can be measured through several methods. Examples of uniformity metrics include low coefficient of variation of pore diameter, basis weight, air permeability, and/or opacity. Uniformity can also mean lack of fiber bundles or roping, or visible holes, or other such defects. Uniformity may also be evaluated by the hydrohead or other liquid barrier measurement of the web. A higher barrier score generally indicates a more uniform web.

Pore diameter can be determined by methods known to those skilled in the art. The mean pore diameter of the nanofiber layer is preferably less than about 15 microns, more preferably less than about 10 microns, and most preferably less than about 5 microns. The desired coefficient of variation for a uniform web can be less than 20%, preferably less than about 15%, and more preferably about 10% or less. The lack of roping can be measured by counting the number of ropes or bundles of fibers in a measured area of the web. The lack of holes can also be measured by counting the number of holes having a diameter above a certain threshold in a measured area of the web. A scanning electron microscope or other enlargement means can be used. For example, the holes may be counted if they are visible to the naked eye using a light box, or are more than 100 microns in diameter.

The method of making the nanofibers of the present invention is preferably a melt fibrillation process, or more preferably a melt film fibrillation process. Generally, this process involves providing a polymeric melt, utilizing a central fluid stream to form a polymeric film, and then using a fluid to form multiple nanofibers from the film. Suitable methods are detailed, for example, in U.S. Pat. No. 4,536,361 to Torobin and U.S. Pat. Nos. 6,382,526, 5,520,425 and 6,695,992 to Reneker. The film may be a hollow tube, relatively flat, or other suitable structure.

As further described in U.S. Pat. No. 4,536,361, the polymer is heated until it forms a liquid and flows easily. The melted polymer may be at a temperature of from about 0° C. to about 400° C., preferably from about 10° C. to about 300° C., and more preferably from about 20° C. to about 220° C. The temperature of the polymer depends on the melting point of the polymer or polymer composition. The temperature of the polymer can be less than about 50° C. above its melting point, preferably less than 25° C. above its melting point, more preferably less than 15° C. above its melting point, and just at or above its melting point or melting range. The melting point or range is measured using ISO 3146 method. The melted polymer will typically have a viscosity of from about 1 Pa-s to about 1000 Pa-s, typically from about 2 to about 200 Pa-s and more commonly from about 4 to about 100 Pa-s. These viscosities are given over a shear rate ranging from about 100 to about 100,000 per second. The melted polymer is at a pressure of about atmospheric pressure or slightly elevated.

In one method, the fiberizing fluid may push through the polymer liquid film to form a hollow polymer tube by blowing and applying pressure on the film and then inner surface of the tube. In another method detailed in U.S. Pat. No. 6,695,992, the fiberizing fluid will form a sheet of thin film from a slit or slot type die design. The fiberizing fluid may be at a temperature close to the temperature of the melted polymer. Non-limiting examples of the fiberizing fluid are gases such as nitrogen or more preferably air. The fiberizing fluid temperature may be a higher temperature than the melted polymer to help in the flow of the polymer and the formation of the hollow tube or flat film. Alternatively, the fiberizing fluid temperature can be below the melted polymer temperature to assist in the formation and solidification of the nanofibers. The fiberizing fluid temperature is less than about 50° C. above the polymer melting point, preferably less than 25° C. above the polymer melting point, more preferably less than 15° C. above the polymer melting point, or just at or above the polymer melting point. The fiberizing fluid temperature may also be below the process temperature, down to 15° C. The pressure of the fiberizing fluid is sufficient to blow the nanofibers and can be slightly above the pressure of the melted polymer as it is extruded out of the orifice.

The fiberizing fluid will generally have a pressure below 5000 psi. Preferably, the fiberizing fluid pressure will be less than 1000 psi, more preferably less than about 100 psi, and most preferably from about 15 to about 80 psi.

The polymer throughput will primarily depend upon the specific polymer used, the nozzle design, and the temperature and pressure of the polymer. The polymer throughput will be more than about 1 gram per minute per orifice. Preferably, the polymer throughput can be more than about 5 gram per minute per orifice and more preferably greater than about 10 gram per minute per orifice. There will likely be several orifices operating at one time which increases the total production throughput. The throughput, along with pressure, temperature, and velocity, are measured at the die orifice exit. Another way to describe the throughput is to use the term of extruded wet length. The polymer throughput will be more than about 0.3 gram per centimeter of extruded wet length. The extruded wet length is defined is the linear distance of the molten film before nanofibers are produced. For example, if the present invention is manifested using discrete nozzles and the nozzle orifice diameter is 1 centimeter, the mass throughput rate for that nozzle is 1 gram/minute, the overall rate is 0.318 gram per cm per minute. Preferably, the polymer throughput will be more than about 3 gram per cm per minute, more preferably greater than about 6 gram per cm per minute, and most preferably greater than 10 gram per cm per minute.

An entraining or other fluid may be used to induce a pulsating or fluctuating pressure field to help in forming a multiplicity of nanofibers. The entraining fluid can be provided by a transverse jet which is located to direct the flow of entraining fluid over and around the film and nanofiber forming region. The entraining fluid can have a velocity of from about 1 to about 100 meter per second and preferably from about 3 to about 50 meter per second. The temperature of the entraining fluid can be the same as the above fiberizing fluid, but it is typically about the same temperature as the melted polymer just as the film is formed. An air curtain or other ancillary air stream can also be used to affect the spray pattern of nanofibers from two or more nozzles. This air stream or curtain may aid in shielding the spray formations between adjacent nozzles or may aid in compressing the spray pattern. The air curtain or stream may improve the uniformity of the web.

Another fluid stream, a quench or heating fluid, can optionally be used. This third fluid stream can be located to direct fluid into the nanofibers to cool or heat the fibers. If the fluid is used as a quenching fluid, it is at a temperature of from about −20° C. to about 100° C. and preferably from about 10°

C. to 40° C. If the fluid is used as a heating fluid, it is at a temperature of from about 40° C. to 400° C. and typically from about 100° C. to about 250° C. Any fluid stream may contribute to the fiberization of the polymer melt and can thus generally be called fiberizing fluids. Any of the fluid streams may contain the treatments or additives for changing the surface, chemical, physical, or mechanical properties of fibers made.

The distance from the orifice or nozzle to collector distance, commonly called die-to-collector distance (DCD), can be optimized. The optimization may aid in producing a more uniform web. A reduction in the DCD may help to reduce the amount of fiber bundling or roping. This lower distance does not enable the fibers to have time to entangle, wrap around one another, or bundle. It may be desired to utilize more than one DCD for a web, to change the DCD during production, or to have different beams with different DCDs. It may be desirable to form a web with different uniformities by changing the DCD.

Nonlimiting examples of other nanofiber making processes from polymeric melts include melt fiber bursting, advanced melt blowing, and fibers splitting from multicomponent fibers and solid films. Examples of melt fiber bursting processes utilizing bursting polymer melt into fine fibers include U.S. Pat. No. 5,075,161 by Nyssen et al.; European Patent Nos. 1 192 301 B1 and 0 724 029 B1 and European Patent Application 1 358 369 A2 by Gerking; and WO 04/020722 by Sodemann et al. These methods utilize Laval nozzles to speed up the gas velocities to sonic and/or supersonic range. When polymer melt is exposed to such high gas velocities, it bursts into multiplicity of fine fibers.

Nyssen et al. disclose in U.S. Pat. No. 5,075,161 a method of bursting polyphenylene sulfide melt into fine filaments. In this method, the Laval nozzle is positioned just after the spinning nozzle. Polymer fibers having an average fiber diameter of less than about 6 microns, preferable from about 0.2 microns to 6 microns, are produced by subjecting the polymer melt streams to drawing out and cooling to below the melt temperature by extruding them into a gaseous medium which flows essentially parallel to the polymer melt streams and attains sonic or supersonic speed. This simultaneous deformation and cooling gives rise to amorphous fine or extremely fine fibers of finite length. High speed fiber bursting minimizes the surface oxidation of the fibers. WO 04/020722 by Sodemann et al. disclose a similar method of producing fine filament spunbonded nonwoven from fiber bursting of thermoplastic polymers by using sonic and supersonic fluid velocities. In said process, the Laval nozzle is placed underneath the spinning nozzle. The spinning speed, melt temperature, and the position of the Laval nozzle are appropriately set to achieve only partial thermal oxidation of fine filaments at their surface. The fibers produced by this method have been disclosed to have diameter of less than 1 micron, and are connected to one another at discrete points. Methods and apparatus disclosed by Gerking in European Patent Applications 1 192 301 B1 and 1 358 369 A2 also utilize Laval nozzle to speed up gas to sonic and supersonic velocity that is used to burst the polymer melt into multiplicity of fine filaments.

Melt film fibrillation process differs from melt fiber bursting process in how the fibers are made and the starting melt geometry from which fine filaments are produced. Melt film fibrillation starts with a film, in some instances a hollow melt film tube, that is thinned by central air jet and then fibrillates into multiplicity of nanofibers. In contrast, the starting melt geometry of melt bursting is a filament melt that when exposed to sonic and supersonic gas velocity in Laval nozzle bursts into multiplicity of nanofibers. Fibrous webs made from the processes may differ in uniformity because of differences in fiber-to-fiber separation and fiber bundle formations.

Various processes and combination of processes can be used to make the webs of the present invention. Preferred methods are methods which produce uniform nanofiber layers. Melt fiber bursting can be combined with melt film fibrillation with two separate beams on a single line. Various aspects of melt fiber bursting could be incorporated into melt film fibrillation. For example, fibers of different strengths and diameters could be produced to provide a desired combination of properties. Alternatively, aspects of melt film fibrillation can be included in other melt fibrillation processes to increase the throughput rate by utilizing a hollow elongated tube to form fibers. For example, a melt film fibrillation process could be modified to include a Laval nozzle to aid in drawing down the fibers. Drawing down can aid in further attenuation and increase the strength of the fibers. This may be particularly preferred for high Tg polymers such as polyesters where crystallization is stress induced.

The nanofibers of the present invention are used to make nonwoven webs suitable for barrier properties in articles. The web is defined as the total nonwoven composite. A web may have one or several layers which are consolidated by thermal point-bonding or other techniques to attain strength, integrity and certain aesthetic characteristics. A layer is the web or part of a web that is produced in a separate fiber lay down or forming step. The webs of the present invention will comprise one or more layers having a significant number of nanofibers having diameters of less than one micron. A significant number is defined as at least about 25%. The significant number of fibers can be at least about 35%, at least about 50%, or more than about 75% of the total number of fibers in the layer. The web could have more than about 90% or about 100% of the fibers having a diameter of less than about one micron. The fiber diameters of the web are measured using a scanning electron microscope at a magnification of greater than about 500 times and up to about 10,000 times as needed for visual analysis. To determine if a significant number of fibers have diameters less than one micron, at least about 100 fibers and preferably more fibers must be measured. The measurements must occur at various regions throughout the layer. Sufficient sampling that is statistically significant must occur.

The fiber diameter of the remaining larger fibers in the nanofiber layer, up to 75%, may have fiber diameters in any range. Typically, the larger fiber diameters will be just above one micron to about 10 microns.

Preferably, a significant number of fibers in a nanofiber layer will have a fiber diameter of less than about 900 nanometers and more preferably from about 100 nanometers to about 900 nanometers. Other preferably ranges of fiber diameter are less than about 700 nanometers and from about 300 to about 900 nanometers. The preferred diameters depend upon the use of the web. It may be desirable to have a significant number of fibers having a diameter of less than about one micron and a significant number of fibers having a diameter of great than about one micron. The larger fibers may trap and immobilize the nanofibers. This may help to reduce the amount of clumping or roping of the nanofibers and prevent the nanofibers from being carried off by stray air currents.

The layer of nanofibers in a web of the present invention may contain more than one polymer. Different polymers or polymer blends may be used for different orifices to produce layers in a web having different fiber diameters and different polymer compositions.

It may be desirable to produce a single layer nonwoven with varying fiber diameters. Alternatively, it can be desired to produce a nonwoven web with multiple layers with each layer having different fiber diameters. The melt film fibrillation process can be modified to produce both small and large diameter fibers to make various webs. The smaller fiber diameters are referred to as having a significant number of fibers having a diameter of less than one micron. The larger diameter fibers include fibers from the melt blowing range (typically 3 to 5 microns) to the spunbond (typically around 10 microns) or any range of fiber diameters above 1 micron. For example, one layer can be produced with an average fiber diameter of less than one micron and another layer with an average fiber diameter of around 5 microns. This type of structure could be used where traditionally spunbond-meltblown-spunbond (SMS) webs are used. The webs with various fiber diameters can be produced on the same line with the same equipment. This is an inexpensive way as the same equipment and components can be used. The operating costs and equipment costs are both controlled. Also, if desired, the same polymer can be used to produce different fiber diameters.

The articles of the present invention will contain the described nonwoven webs. The web may comprise the entire articles, such as a wipe, or the web may comprise one component of the article, such as a diaper. Hygiene articles are preferred articles. The hygiene articles include diapers, training pants, adult incontinence pads, catamenials products such as feminine care pads and pantiliners, tampons, personal cleansing articles, personal care articles, and personal care wipes including baby wipes, facial wipes, body wipes, and feminine wipes. Personal care articles include articles such as wound dressings, active delivery wraps or patches, and other substrates that are applied to the body, particularly the skin. Disposable underwear or clothing and protective wear for personal or industrial uses may also be desired. Other uses of wipes can be clean room wipes or decontamination wipes for use to absorb or control spills and other industrial wipes.

In a diaper, the web may be used as a barrier layer such as a barrier-on-core or an outercover. The webs may also be used as a high barrier cuff with a high hydrostatic head to enable low leakage incident rates of thin, narrow crotch diapers desired for comfort and fit. A typical web utilizing nanofibers is a web wherein the nanofiber layer is combined with at least one spunbond layer and consolidated using thermal point-bonding, hydro-entangling or other techniques suitable and appropriate for the end-use. There may be one or two spunbond layers encompassing the nanofiber layer.

In a diaper or other disposable absorbent product, the nonwoven web containing nanofibers may be utilized as a barrier layer. The barrier layer may be disposed between an absorbent core and an outer layer containing a garment. The absorbent core is the component of the article that is primarily responsible for fluid handling properties such as acquiring, transporting, distributing, and storing body fluids. The absorbent core is typically located between a liquid pervious body-side inner layer and a vapor permeable, liquid impermeable outer cover. The outer layer, also known as the back sheet or outer covering, is located on the outside of the disposable product. In the case of a diaper, the outer layer contacts the user's garment or clothing. The barrier layer may alternatively or also be disposed between the absorbent core and an inner layer. The inner layer, also known as a top sheet, is located on the side closest to the user's skin. The inner layer may contact the user's skin or may contact a separate top sheet with contacts the user's skin. The barrier layer may be absorbent. The barrier layer most preferably has a balance between convective air flow and absorptive barrier property. The convective air flow property is effective to reduce the relative humidity within the space between the absorbent article and the wearer's skin. The combination of liquid absorption and liquid barrier property provides protection against the wet through problem and is especially beneficial when the absorbent article is under impact and/or sustained pressure. Further description and benefits of the barrier layers may be found in WO 01/97731.

The webs may be used in wipes to enable improved lotion handling and reduced gradient of liquids. The webs may also provide controlled delivery of a substance. The delivered substance can be of liquids, lotions, actives, or other materials. Due to the high surface area of the nanofibers, the webs may be used as absorbent materials for wipes or cores of feminine care product pads, diapers, training pants, or adult incontinence. The webs may provide enhanced distribution of fluids and/or retention. Additionally, the webs for absorbent uses may be made with added particulates or absorbent or natural fibers for increased absorbance or certain layers of the webs may have different properties.

The nanofiber webs may also be used in articles wherein opaqueness is desired. Added opaqueness may result due to the small fiber diameter and uniformity or pigments may be added to the polymer melt or webs. The webs have also been found to have low linting. This may be due to longer length fibers or entangling of fibers in the web.

Other products that will benefit from a nanofiber web include filters. Filters can be for industrial, personal, or home use and can be used to filter air, liquids, or small particles. Industrial uses can include automotive, furnace, water, and other types of filters. A type of personal filter includes a filter mask such as a surgical mask. Other medical uses of webs containing nanofiber layers include surgical gowns, wound dressings, and medical barriers. The webs can also be used as noise and thermal insulators, for outdoor gear, clothing, and as conducting fibers.

EXAMPLES

Comparative Example 1

Basell Profax PH-835, a polypropylene polymer with Tg of 6° C., as determined by differential scanning calorimetry. The process temperature is 280° C. with the fiberizing fluid temperature of 25° C.

Comparative Example 2

Dow Chemical Company Aspun 6811A, nominally a 27 melt index polyethylene with Tg of −15° C. was run. The material would not fibrillate and form nanofibers under any conditions.

Example 1

Biomer L9000, nominally a 17 melt flow rate polylacticacid polymer has a Tg of 55° C. The material could be fibrillated and formed into nanofibers. The process temperature is 280° C. with the fiberizing fluid temperature of 25° C.

Example 2

Dow Chemical Company Styron A-Tech 6079 with a typical Tg of 100° C., a polystyrene, can be used to produce nanofibers. The process temperature is 280° C. with the fiberizing fluid temperature of 25° C.

Example 3

Dow Chemical Company CALIBRE 200-15 with a typical Tg of 150° C., a polycarbonate, can be used to produce nanofibers. The process temperature is 280° C. with the fiberizing fluid temperature of 25° C.

Example 4

DuPont Zytel Type 101 with a typical Tg of 50° C., a polyamide, can be used to produce nanofibers. The process temperature is 300° C. with the fiberizing fluid temperature of 25° C.

Example 5

Eastman Chemical Company Eastman F61HC with a typical Tg of 80° C., a crystallizable poly(ester terephthalate), can be used to produce nanofibers. The process temperature is 300° C. with the fiberizing fluid temperature of 25° C.

Example 6

Eastman Chemical Company copolyester 14285 with a typical Tg of 80° C., an amorphous poly(ester terephthalate), can be used to produce nanofibers. The process temperature is 300° C. with the fiberizing fluid temperature of 25° C.

All documents cited are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A nonwoven web comprising at least one nanofiber layer having a significant number of nanofibers with diameters less than about one micron and having an average pore diameter of less than 15 microns, wherein the nanofiber layer comprises nanofibers formed from a high glass transition temperature polymer and nanofibers formed from a low glass transition temperature polymer, wherein the high glass transition temperature polymer is selected from the group consisting of polylactic acid, polystyrene, polyamide, polyester, and thermoplastic starch and the glass transition temperature of the high glass transition temperature polymer is greater than about 25° C. and wherein the low glass transition polymer is selected from the group consisting of polypropylene and polyethylene.

2. The nonwoven web according to claim 1 wherein the high glass transition temperature polymer has a glass transition temperature greater than about 30° C.

3. The nonwoven web of claim 1 wherein the nanofiber layer has at least about 50% of nanofibers with a diameter of less than about one micron.

4. The nonwoven web of claim 1 wherein the nanofiber layer has a basis weight of from about 0.5 gsm to about 15 gsm.

5. The nonwoven web of claim 1 wherein the high glass transition temperature polymer has a glass transition temperature greater than about 40° C.

6. An article comprising a nonwoven web of claim 1.

7. The article of claim 6 wherein the article is selected from the group consisting of diapers, training pants, adult incontinence pads, catamenials products such as feminine care pads and pantiliners, tampons, personal cleansing articles, personal care articles, and personal care wipes such as baby wipes, facial wipes, body wipes and feminine wipes, and combinations thereof.

8. The article of claim 7 wherein the nonwoven web is a barrier layer.

9. A nonwoven web comprising at least one nanofiber layer having an average pore diameter of less than 15 microns and having a significant number of nanofibers with diameters less than about one micron, the nanofiber layer having distinct areas comprising nanofibers formed from different glass transition temperature polymers wherein the nanofibers in each area comprises either high or low glass transition temperature polymers, wherein the high glass transition temperature polymer is selected from the group consisting of polylactic acid, polystyrene, polyamide, polyester, and thermoplastic starch and the glass transition temperature of the high glass transition temperature polymer is greater than about 25° C. and wherein the low glass transition polymer is selected from the group consisting of polypropylene and polyethylene.

10. A self sticking web comprising at least one nanofiber layer having a significant number of nanofibers with diameters less than about one micron, wherein some of the nanofibers are made from a high glass transition temperature polymer and some of the nanofibers are made from a low glass transition temperature polymer, wherein the high glass transition temperature polymer is selected from the group consisting of polylactic acid, polystyrene, polyamide, polyester, and thermoplastic starch and the glass transition temperature of the high glass transition temperature polymer is greater than about 25° C. and wherein the low glass transition polymer is selected from the group consisting of polypropylene and polyethylene.

* * * * *